(12) United States Patent
Benzerrouk et al.

(10) Patent No.: US 8,581,975 B2
(45) Date of Patent: Nov. 12, 2013

(54) INFRARED DEFECT DETECTION SYSTEM AND METHOD FOR THE EVALUATION OF POWDERMETALLIC COMPACTS

(75) Inventors: Souheil Benzerrouk, Lowell, MA (US); Reinhold Ludwig, Paxton, MA (US); Diran Apelian, West Boylston, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 897 days.

(21) Appl. No.: 12/304,520

(22) PCT Filed: Jun. 18, 2007

(86) PCT No.: PCT/US2007/071451
§ 371 (c)(1),
(2), (4) Date: Oct. 15, 2009

(87) PCT Pub. No.: WO2007/147158
PCT Pub. Date: Dec. 21, 2007

(65) Prior Publication Data
US 2010/0033565 A1    Feb. 11, 2010

Related U.S. Application Data

(60) Provisional application No. 60/814,451, filed on Jun. 16, 2006.

(51) Int. Cl.
*H04N 7/18* (2006.01)
(52) U.S. Cl.
USPC .......... 348/125; 348/126; 348/127; 348/128; 348/129; 348/130; 348/131; 382/152

(58) Field of Classification Search
USPC ................... 348/125–131; 382/152
See application file for complete search history.

(56) References Cited

U.S. PATENT DOCUMENTS

| | | | |
|---|---|---|---|
| 3,609,532 A * | 9/1971 | Van Kirk et al. | 324/215 |
| 4,024,470 A * | 5/1977 | Vild et al. | 324/224 |
| 4,647,220 A * | 3/1987 | Adams et al. | 374/5 |
| 4,724,482 A * | 2/1988 | Duvent | 348/164 |
| 5,386,117 A * | 1/1995 | Piety et al. | 250/330 |
| 5,483,604 A * | 1/1996 | Salisbury | 382/152 |
| 5,637,871 A * | 6/1997 | Piety et al. | 250/330 |
| 5,719,395 A * | 2/1998 | Lesniak | 250/330 |
| 5,834,661 A * | 11/1998 | Nonaka et al. | 73/866 |
| 5,911,941 A | 6/1999 | Rokhvarger et al. | |
| 5,994,699 A * | 11/1999 | Akagawa | 250/332 |
| 6,751,342 B2 * | 6/2004 | Shepard | 382/141 |
| 6,840,666 B2 * | 1/2005 | Enachescu et al. | 374/5 |
| 6,943,558 B2 | 9/2005 | Hale et al. | |

(Continued)

OTHER PUBLICATIONS

ISR/WO for International Application # PCT/US07/71451, mailed Feb. 12, 2008, Worcester Polytechnic Institute, International Filing Date Jun. 18, 2007.

(Continued)

*Primary Examiner* — Duyen Doan
(74) *Attorney, Agent, or Firm* — Burns & Levinson, LLP; Jacob N. Erlich, Esq.; Marlo Schepper Grolnic

(57) ABSTRACT

A pulsed thermography defect detection apparatus including active and passive infrared (IR) thermography for non-destructive testing (NDT) of powdermetallic (P/M) components for on-line and off-line inspection.

20 Claims, 15 Drawing Sheets

(56) References Cited

U.S. PATENT DOCUMENTS

| | | | |
|---|---|---|---|
| 7,067,011 B2* | 6/2006 | Inoue et al. | 118/638 |
| 7,276,698 B2* | 10/2007 | Tohyama et al. | 250/338.1 |
| 7,454,050 B2* | 11/2008 | Garvey | 382/141 |
| 2003/0219059 A1* | 11/2003 | Scott | 374/5 |
| 2004/0052296 A1* | 3/2004 | Kubal et al. | 374/120 |
| 2005/0186327 A1* | 8/2005 | Saito et al. | 427/8 |
| 2008/0067455 A1* | 3/2008 | Zombo et al. | 250/504 R |

OTHER PUBLICATIONS

International Search Report dated Feb. 12, 2008 for PCT/US07/71451 filed Jun. 18, 2007. Applicant: Worcester Polytechnic Institute.

U.S. Appl. No. 60/814,451, filed Jun. 16, 2006. Applicants: Souheil Benzerrouk et al. Title: Infrared Defect Detection System and Method for the Evaluation of Powerdermetallic Compacts.

* cited by examiner

Start defects　　　　　　　　　　　　End defects

INFRARED DEFECT DETECTION SYSTEM AND METHOD FOR THE EVALUATION OF POWDERMETALLIC COMPACTS

CROSS REFERENCE TO RELATED APPLICATIONS

This application claims priority to the prior patent application entitled, INFRARED DEFECT DETECTION SYSTEM AND METHOD FOR THE EVALUATION OF POWDERMETALLIC COMPONENTS, having a Ser. No. 60/814,451 and that was filed in the United States Patent and Trademark Office on Jun. 16, 2006.

FIELD OF THE INVENTION

The present invention relates generally to the field of detecting defects in manufactured parts and in particular to detecting defects in parts manufactured using powder metallurgy techniques.

BACKGROUND OF THE INVENTION

To meet today's market requirements, metal parts manufacturers are turning to new technologies and processes as well as new implementations. Among these processes is the powdermetallic (P/M) production where low cost, high volume precision parts are efficiently manufactured. This process along with its benefits brings new challenges, including the need for a full quality assessment and control of each part, in other words one hundred percent testing. The ability to directly detect flaws as early as possible in the manufacturing cycle, in conjunction with the possibility to perform in-situ evaluations of components, will reduce overhead and improve yield. Today's process lacks this ability and relies only on indirect methods such as the measurement of weight along with statistical sampling to perform more comprehensive part evaluation through the measurement of density and using destructive methods to study the integrity.

For the above reasons, it would be beneficial to provide an apparatus and method for testing powder metallurgy parts directly and early in the manufacturing cycle.

SUMMARY OF THE INVENTION

A pulsed thermography defect detection is described that includes active and passive thermography for non-destructive testing (NDT) of powdermetallic (P/M) components for on-line and off-line inspection. The electric Joule heating effect in the sample under test, caused by either direct current (DC) or alternate current (AC), is used to generate a temperature profile throughout the P/M sample. Recording the surface temperature distribution with an infrared (IR) camera provides information that can be collected for the integrity and quality assessment of the samples. In addition, pulsed thermography is utilized whereby the sample is excited with a current pulse and the thermal response is recorded over time. Specifically, the IR imaging of sub-surface defects is based on a transient temperature recording approach that uses an electric control system to synchronize and monitor the thermal response due to an electrically generated heat source. This enhances the detection capabilities to include subsurface defects and relatively small surface and subsurface defects.

The P/M components may be in the pre-sinter (or green) state in an on-line manufacturing environment to ensure a substantially high percent quality assurance that may approach 100%. The inspection approach being developed may be used to test all green-state components as they exit the componention press at speeds of up to 1,000 parts per hour. Tests may be carried out for a statistical quality analysis on the components.

The pulsed thermography system described herein detects surface and subsurface defects in P/M components. In one embodiment, the pulsed thermography system includes a power source coupled to a powdermetallic component under test and provides an electric current to the powdermetallic component that is used to electrically heat it. A function generator, or a timing generator, is coupled to the power source and controls the shape and duration of the pulse or pluses of the electric current applied to the component. An infrared camera is optically coupled to the powdermetallic component and records an image of the heated component at infrared frequencies, and wherein the infrared camera further is controlled by the function generator. A signal processing system is coupled to the infrared camera and receives the recorded image and then processes the recorded image to detect flaws in the powdermetallic component. The power source may be a direct current (DC) current source or an alternating current (AC) current source of variable frequency. In addition, the present invention may include a switch for controlling the electric current under the control of the function generator that is coupled to the switch. The switch may be a solid state switching device and in particular, a so-called MOSFET or IGBT device. The present invention may include first and second electrode contacts that sandwich the component between them. The first and second electrode contacts are coupled to the power source and are sized and configured to provide substantially uniform current flow into the powdermetallic component. The present invention may also include a press drive system attached to the first and/or second contact and able to provide a biasing force against the contact(s) to maintain a consistent electrical connectivity between the contact(s) and the powdermetallic component.

In the event that AC current is used, the frequency of the AC current driving the induction coil is selected to provide a desired depth of penetration of the induced eddy currents in the powdermetallic component. The induction coil may be coupled to the AC power source, to induce electric currents in the powdermetallic component. An insulating platform may also be disposed between the induction coil and the powdermetallic component.

Alternatively, passive thermography may be used in which the heat remaining in a component after processing provides the heat that is sensed by the infrared camera.

The signal processing system receives an infrared image of the component and analyzes the image using threshold processing or profile processing. Threshold processing includes subtracting a threshold value from the value of each pixel in the image. Profile processing includes using two or more profiles on the surface of the powdermetallic component and separating thermal gradients generated by the defects from other effects by subtracting a first profile thermal gradient from a second profile thermal gradient. The analysis of the image may also include calculating the derivative of a thermal profile of a plurality of preselected areas on the surface of the powdermetallic component and/or calculating the so-called Laplacian of a thermal profile of a plurality of preselected areas on the surface of the powdermetallic component.

A method is also provided for using pulsed thermography to detect defects in a powdermetallic component comprising the steps of first injecting an electric current into the powdermetallic component and second inducing a temperature change in the powdermetallic component. One or more infrared images of the heated powdermetallic component are captured and analyzed to detect temperature differences that may be indicia of a defect in the powdermetallic component. The method may also include injecting a direct current (DC) into the component such that the powdermetallic component has substantially uniform current flow therethrough, or injecting an alternating current (AC) having a frequency selected to provide a desired penetration depth of the alternating current into the powdermetallic component. The AC current may be induced into the powdermetallic component via an induction coil or other induction apparatus. The captured infrared image may be analyzed by determining the thermal gradient on two or more profiles defined on the surface of the powdermetallic component and separating thermal gradients generated by the defects from other effects by subtracting a first profile thermal gradient from a second profile thermal gradient. Alternatively, the infrared image may be analyzed by determining the derivative of a thermal profile of one or more preselected areas on the surface of the powdermetallic component, determining the Laplacian of a thermal profile of a plurality of one or more preselected areas on the surface of the powdermetallic component, or a combination of these methods.

BRIEF DESCRIPTION OF THE DRAWINGS

For a better understanding of the present invention, together with other and further objects thereof, reference is made to the accompanying drawings and detailed description and its scope will be pointed out in the appended claims.

DETAILED DESCRIPTION OF THE INVENTION

Figure 1:
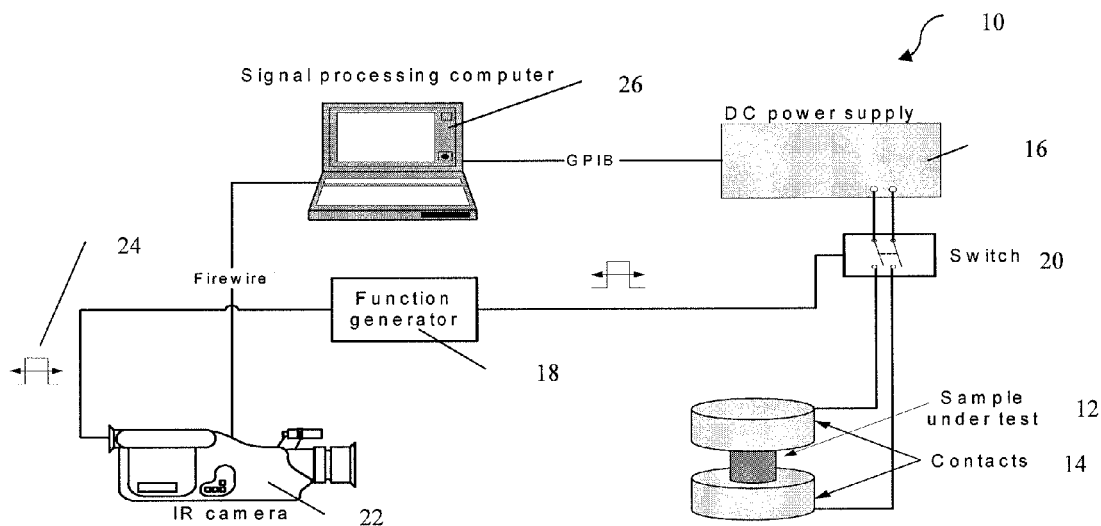
FIG. 1 shows a dynamic IR test system constructed in accordance with one embodiment of the present invention.

FIG. 1 depicts a pulsed thermography apparatus for detecting defects in a powdermetallic component according to an embodiment of the present invention. As used herein, powder metallic components includes powder metallic compacts as well as other powder metallic parts. In particular, the apparatus 10 includes a powdermetallic component 12, which is the object under test, sandwiched between first and second electric contacts 14. A direct current (DC) power source 16 is coupled to the first and second electric contacts 14, via switch 20, to provide current injection into the component 12. The component 12 is heated by the injected current and emits infrared radiation that varies according to the temperature in known relationships. An infrared camera 22 is configured and oriented such that the component 12 is within the infrared camera's field of view. During the process of heating component 12, the infrared camera 22 records one or more images of the component 12, typically within the 8-12 um wavelength range. A function generator 18 controls the switch 20 and the operation of the infrared camera 20 using either a pulse or a step-function transient signal 24, where the leading edge of the pulse or step-function is used as trigger of the infrared camera 20 to start recording and for the switch 20 to switch to a conductive state. The function generator may also be a timing signal generator. Typically, the switch 20 is a solid state device, such as a metal oxide semiconductor field effect transistor (MOSFET) or insulated gate bipolar transistor (IGBT) switch, which is used to shape the current waveform as needed and to maintain the fall and rise time of the electric current within certain parameters. The signal processing system 26 is coupled to both the power source 16 to control the electric current level and the infrared camera 20 to control the capturing of images during the testing process.

Figure 2:
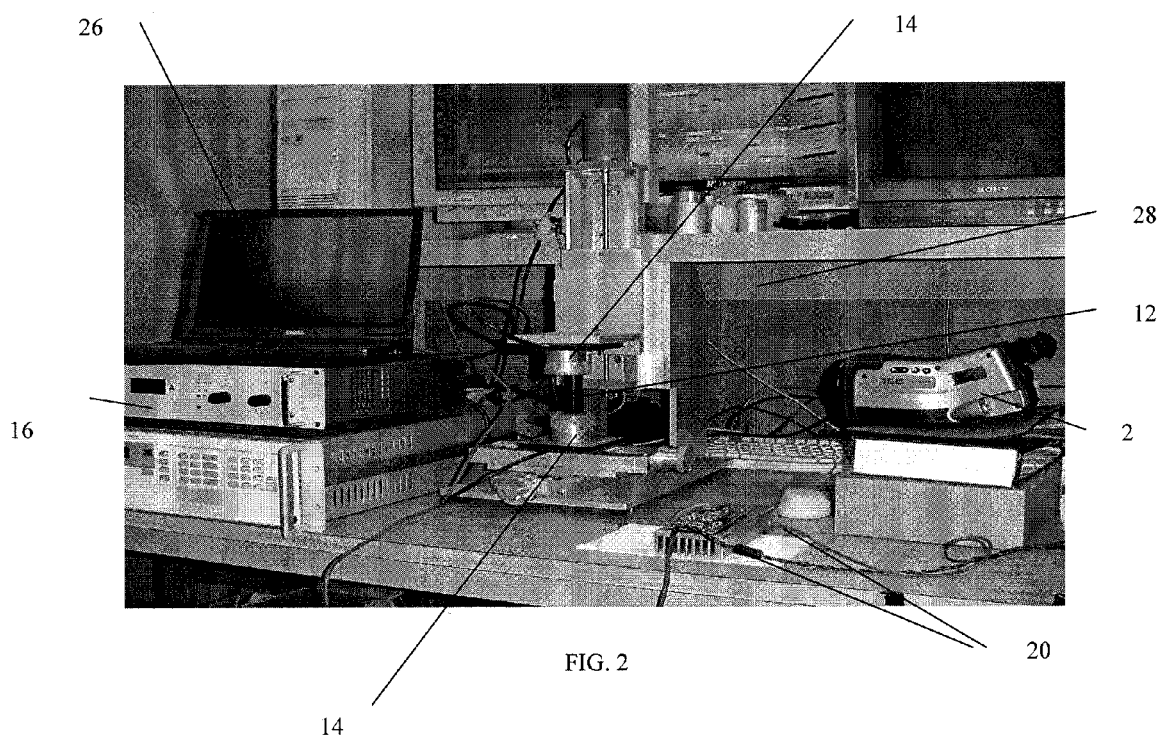
FIG. 2 is a photograph of the system of FIG. 1 showing the camera, the electric contacts and the switching circuit.

FIG. 2 depicts a physically realized system that includes large aluminum contacts that are selected in size to provide a substantially uniform electric current flowing into the component 12. A substantially uniform electric current is needed to ensure that the component 12 is uniformly heated via Joule heating. In addition, FIG. 2 further includes a press system 28 that has been integrated to the aluminum contacts to maintain a constant and consistent electric connection between the component 12 and the electrical contacts 14. The press system 28 may include a stepper motor coupled to one or both of the electrical contacts 14.

Figure 3:
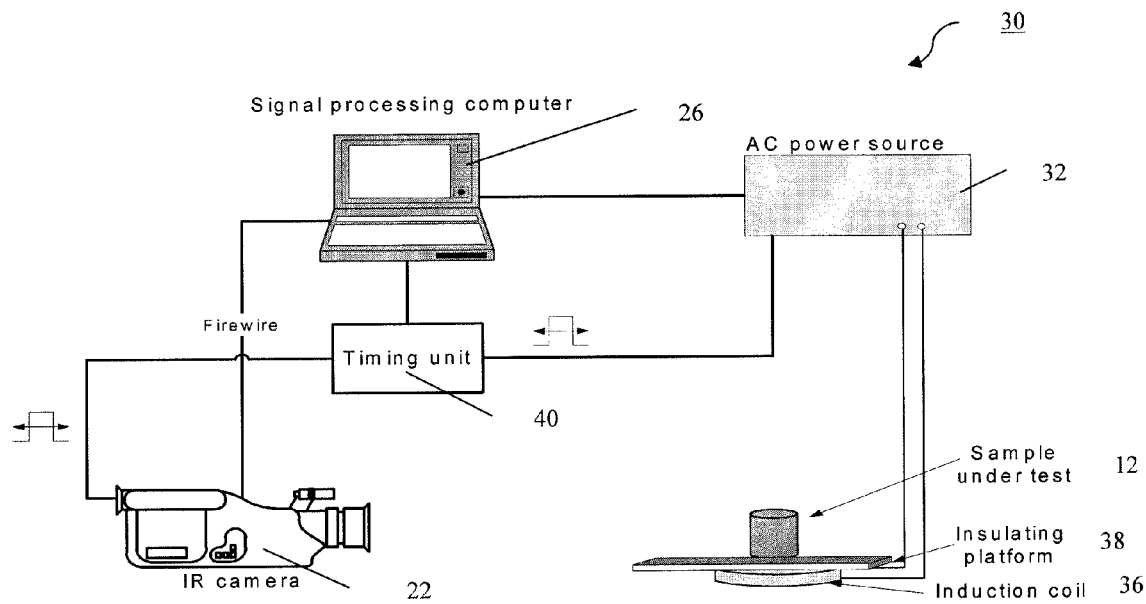
FIG. 3 shows a system constructed in accordance with another embodiment of the present disclosure to conduct dynamic recording with an induction heating source.

FIG. 3 depicts an apparatus for detecting defects in a powdermetallic component according to another embodiment of the present invention. In particular, the apparatus 30 includes a powdermetallic component 12, which is the object under test, disposed upon an insulating platform 38. An alternating current (AC) power source 32 is coupled to an induction coil 36, to provide induced electrical currents within the component 12. The frequency of the AC current is selected as a function of the desired depth of penetration of the induced eddy currents within the component 12 and the material that the component 12 is comprised of. Typically, the frequency is selected to ensure that the electric current flows at or near the surface of component 12. In this way, the thermal signature of a defect is raised to a detectable level. The component 12 is heated by the induced current and emits infrared radiation that varies according to the temperature in a known relationship. An infrared camera 22 is configured and oriented such that the component 12 is within the infrared camera's field of view. During the process of heating component 12, the infrared camera 22 records one or more images of the component 12, typically within the 8-12 um wavelength range. A timing generator 40 provides timing pulses to control the AC power source 32 and the operation of the infrared camera 22, where the leading edge of the timing pulse is used a s trigger the infrared camera 20 to start recording and for the AC power source 32 to provide current to the induction heating system 34. The signal processing system 26 is coupled to the AC power source 32 to control the electric current level, the infrared camera 20 to control the capturing of images during the testing process, and the timing unit for the necessary clocking signals. Additionally, the parts may be moved past the camera using a conveyer system, wherein the conveyer system is part of the insulating platform.

Figure 4:
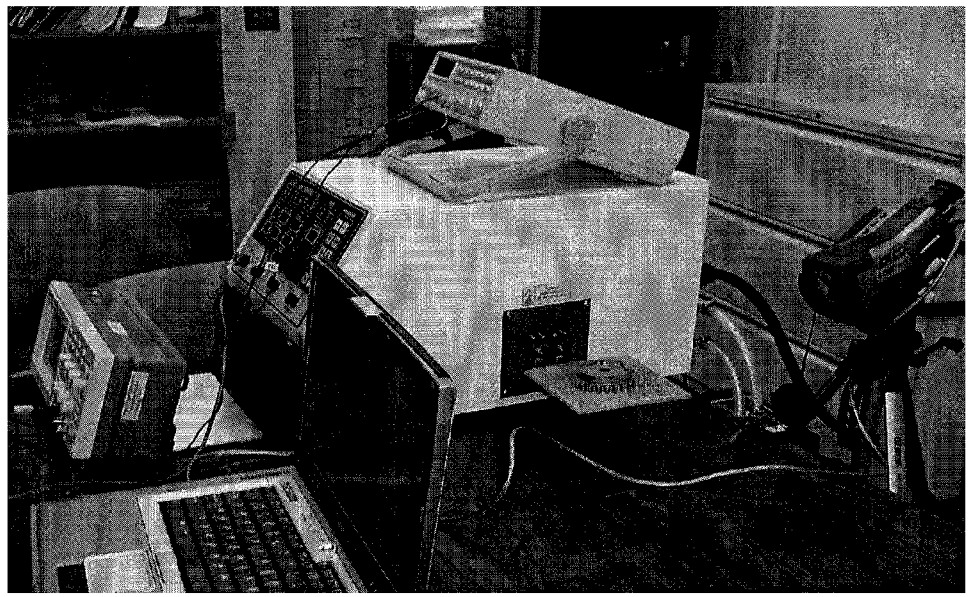
FIG. 4 is a photograph of the system of FIG. 3.

FIG. 4 depicts a photograph of the system of FIG. 3 and in particular, provides additional details for the induction heating system 34, including insulating platform 38.

Figure 5:
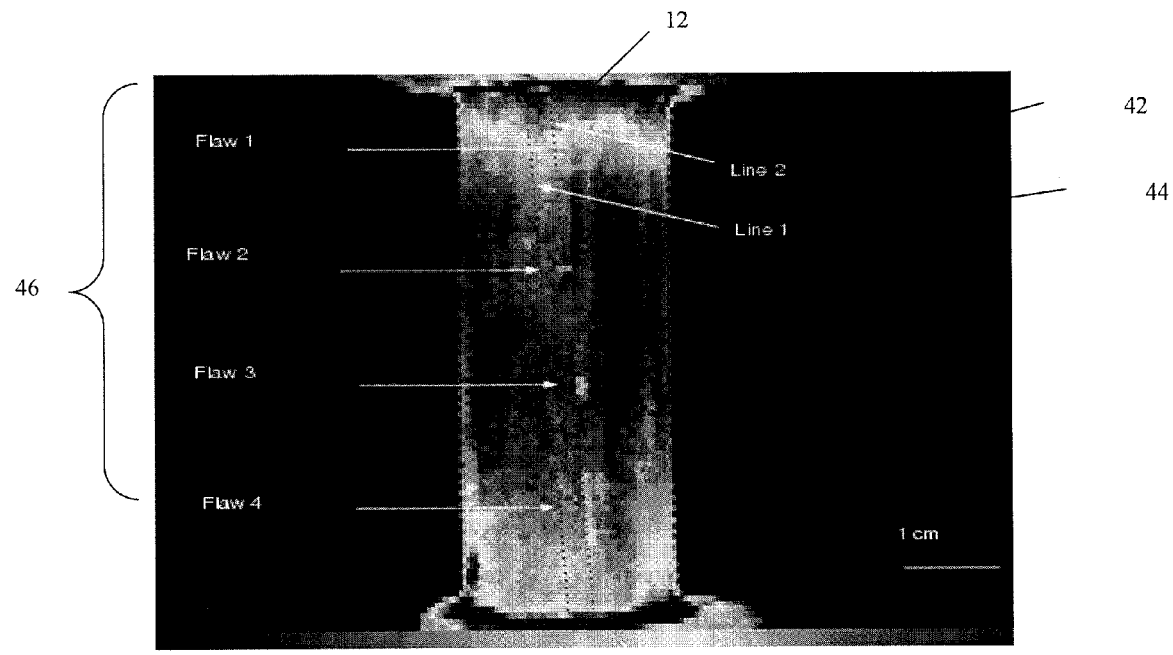
FIG. 5 shows an IR image recording from a cylindrical green-state component with four artificially created surface-breaking defects.

FIG. 5 depicts a thermal image of a cylindrical shaped P/M component subject to DC current excitation by system 10, as described above with reference to FIGS. 1 and 2. In an effort to evaluate the effects of flaw size, shape, and orientation, a number of defects were artificially created in the P/M component 12 with the aid of a knife. The dimensions of those defects are listed in Table 1.

TABLE 1

Flaw parameters in green-state cylindrical parts (the location is defined as distance from the top).

| Flaw # | Length [mm] | Width [µm] | Depth [µm] | Orientation | Location [mm] |
|---|---|---|---|---|---|
| 1 | 10 | <20 | <20 | Horizontal | 10 |
| 2 | 1 | 20 | 20 | Horizontal | 20 |
| 3 | 2 | 20 | 20 | Vertical | 30 |
| 4 | 10 | <20 | <20 | Vertical | 50 |

These defects were created in a cylindrical P/M component 12 consisting of 1000 B iron powder without lubricant. The component 12 was then subjected to a DC current flow of 20 A. The infrared image, depicted in FIG. 5, was acquired by camera 22, stored in the signal processing computer 26, and post-processed by the signal processing computer using one or more image analysis techniques such as profiling and thresholding. In one embodiment, the image is recorded in an index image format, which is transformed in camera 22 to a gray-scale where each pixel has a value ranging from 0 (no intensity) to 255 (full intensity). The image may be stored as an intensity matrix where the value of each pixel is stored in the matrix. This image may then be paletted for viewing using a simple coloring scheme where the base temperature is encoded in green, cooler areas are represented in blue, and hot spots are displayed in red.

Figure 6:
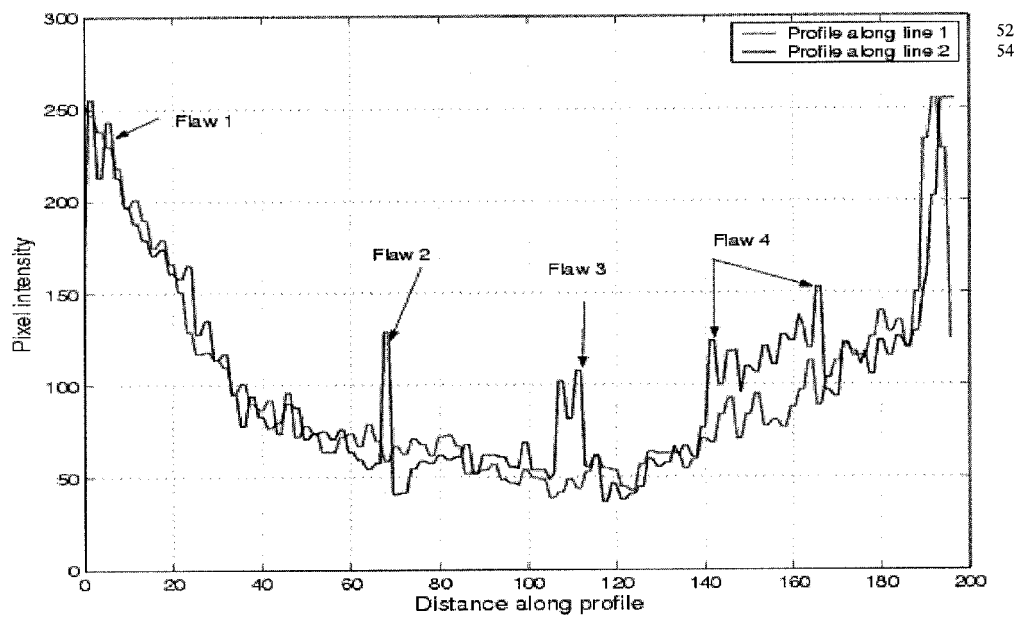
FIG. 6 shows a plot of pixel intensity along the two dotted lines in FIG. 5, with a spatial pixel to pixel distance of 300 μm.
Figure 7:
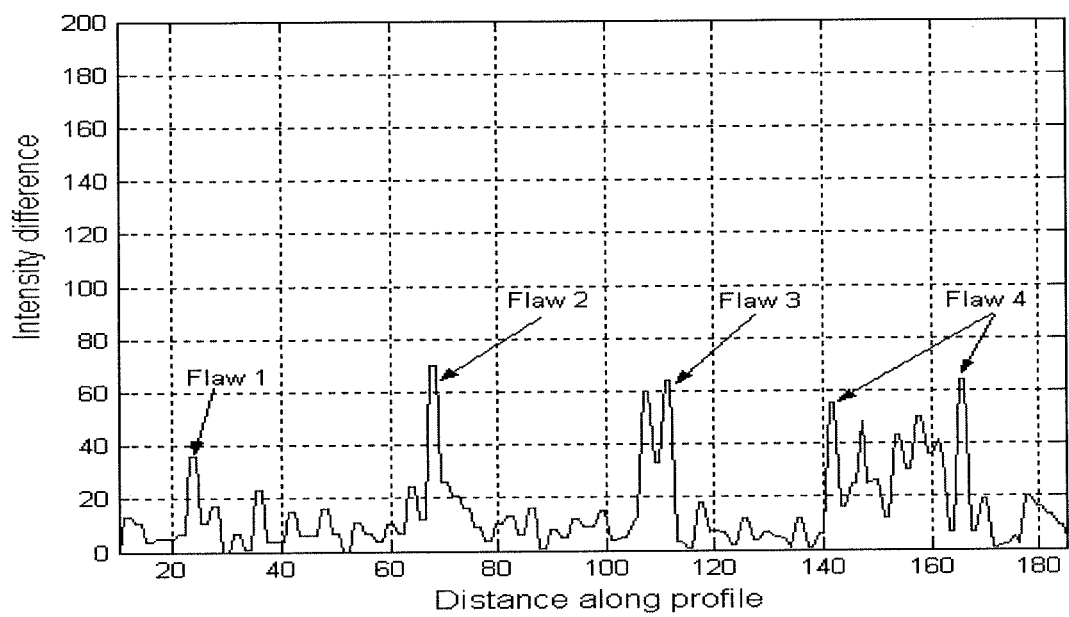
FIG. 7 shows a plot of the difference in intensity between adjacent pixels along Line 1 and Line 2 shown in FIG. 6.

As depicted in FIG. 5, the defects 46 are disposed on the surface of component 12. To quantify the temperature gradient caused by the presence of one of the defects 46, a path 42 on the surface of component 12 is selected and the temperature profile is generated along the path 42. A path 44 is also selected, where the path 44 is a path clear of defects and parallel to the path 42. A temperature profile is then generated for the path 44. FIG. 6 depicts the temperature profiles along paths 42 and 44. While it is apparent from FIG. 6 that path 42 has defects, as shown by the large deviations in temperature at particular locations, post processing is needed to ensure that the defects are detected In the post-processing step, the thermal gradients generated by the defects are separated from the effects of material density variations, contact resistance and reflections. FIG. 7 shows a difference plot, where intensity values along Line 42 have been subtracted from values along Line 44, resulting in the profile shown. As depicted in FIG. 7, the defects 46 are clearly identifiable due to the intensity difference between the paths 42 and 44.

Figure 8A:
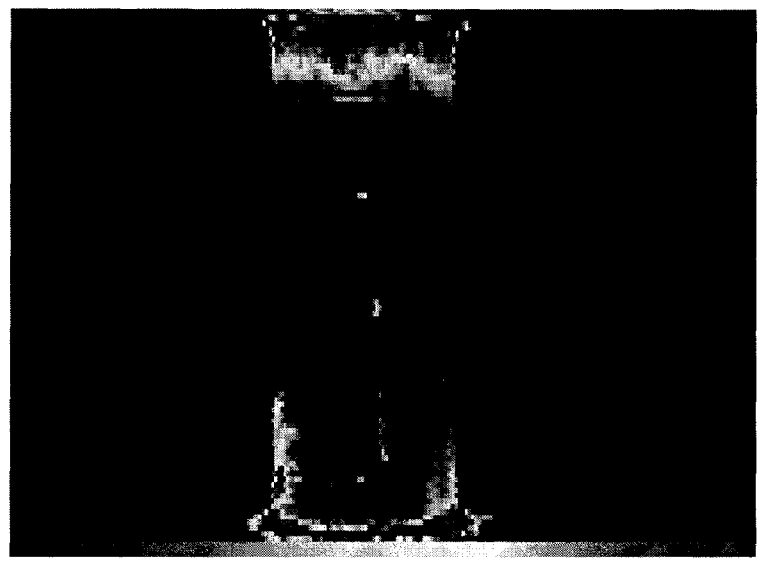
FIG. 8(a) shows an IR image of the cylindrical part of FIGS. 1 and 5 after thresholding.
Figure 8B:
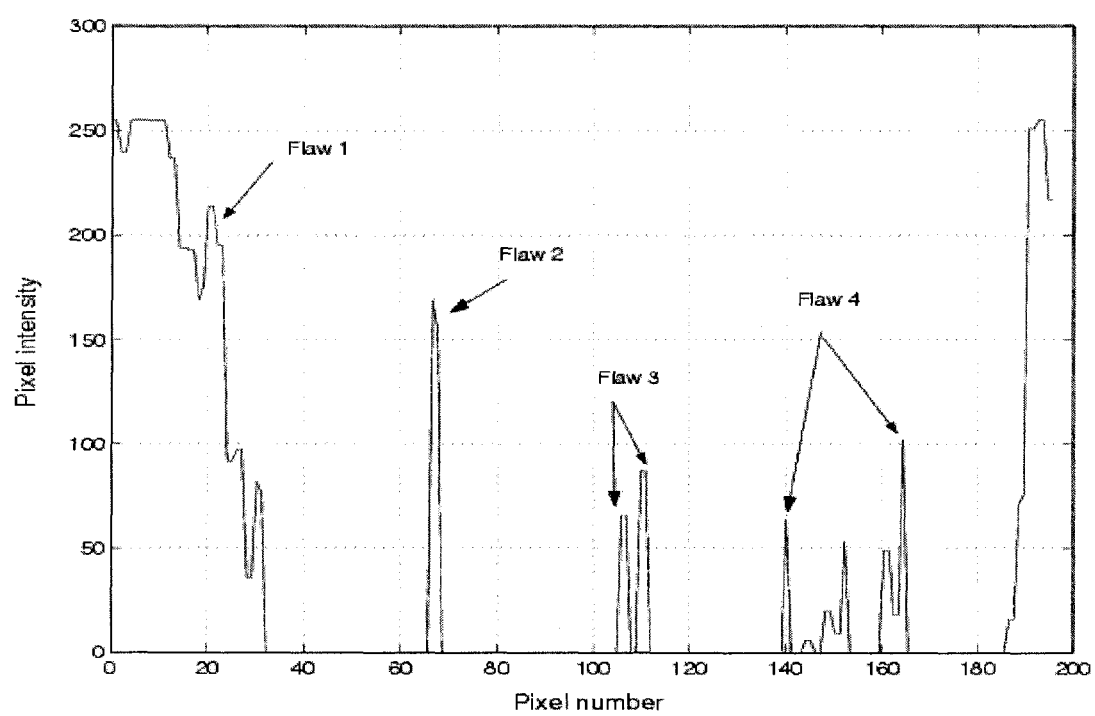
FIG. 8(b) shows a profile along the centerline with a spatial pixel-to-pixel distance of 300 μm.

In one embodiment, a simple thresholding concept can be applied to the raw intensity data depicted in FIG. 6. In this embodiment, any areas with intensities below a preset value are set to zero. Areas with intensities above the preset value are assigned their intensity value. In one embodiment, the pixels having an intensity below the threshold value are set to black and the pixels having an intensity above the threshold value are set to a "bright" value. FIG. 8a depicts an image of the component 12 during heating, where the intensity data has been filtered using a threshold filter, in which pixels below the preset value are set to 0, i.e., black, and the pixels having a value above the preset value are set to a "bright" value. As can be seen in FIG. 8a, all four of the defects introduced to the component 12, and described in Table 1 above, are visible.

Many algorithms may be used to automate this operation. A convenient scheme utilizes the histogram (a representation of the number of pixels at each level), while more elaborate algorithms use contextual and statistical information including information from adjacent pixels. The choice of a particular algorithm is based upon the particular physical characteristics of the component 12, the materials used to form the component 12, and other system requirements. In addition, any number of profile paths may be used to examine the parts for defects and two profile paths was shown for exemplary purposes only and is not meant to be limiting.

Although the system 10 described above employs basic image analysis techniques, a fault detection system according to the present disclosure could additionally employ a graphical display whereby the captured thermal image is visualized, and an image processing and evaluation algorithm is employed that can be used to assess the integrity of the sample from the captured image.

Figure 9:
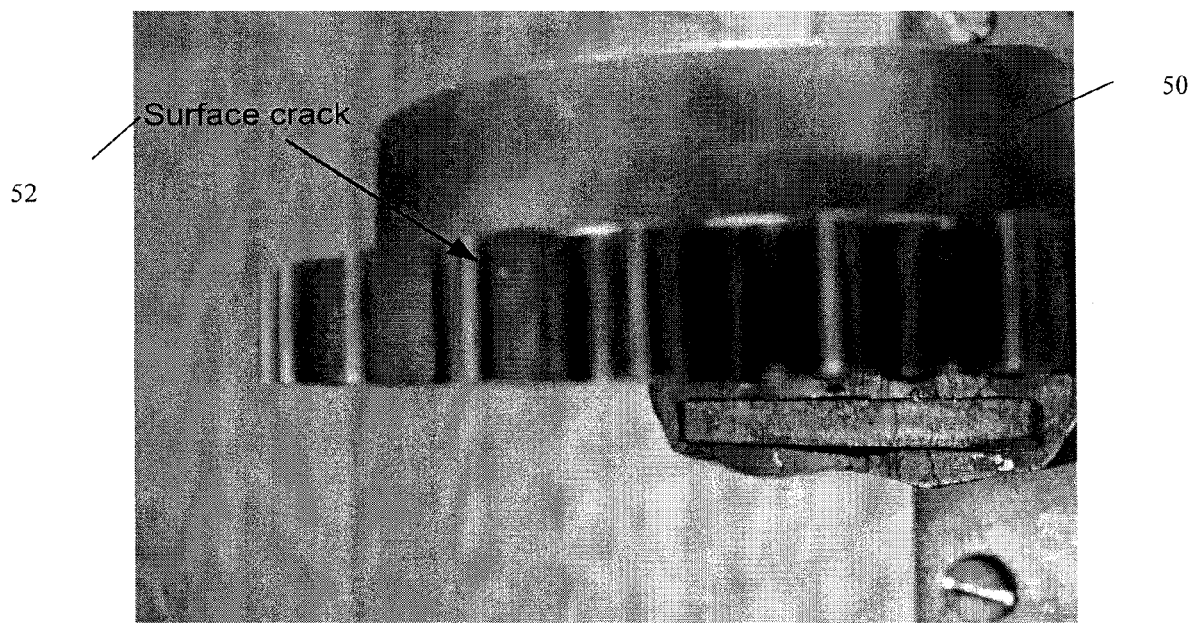
FIG. 9 shows a P/M gear component with a surface crack situated on the tooth surface.

The component 12 used in FIGS. 5-8 above was a simple cylinder having no protrusions, crevices, or other complex shapes. FIG. 9 depicts a P/M gear component that presents a more complex geometric shape and is therefore it is more difficult to detect defects in this component. In particular, the gear teeth cause non-uniform density distributions in the part, which in turn causes reflections of heat, which depending on the orientation of the gear component and infrared camera may result in either areas being colder or warmer than the surrounding material. In addition, the multilevel nature of the part also makes it prone to corner cracks 52 which cannot easily be detected as a result of complicated heat transfer mechanisms at the corner. The steel powder gear component 50 used as an example in this embodiment is constructed with 1.0% Cu, 0.2% C and lubricated with 0.8% wax. The density ranges from 6.8 g/cm$^3$ to 7.1 g/cm$^3$.

The geometry of the gear depicted in FIG. 9, and in general any other complex geometric shaped part, makes it difficult to ensure that a DC current used to heat the component has substantially uniform current throughout the part. As discussed above, uniform current is desirable so that the entire component is heated substantially uniformly. To ensure a substantially uniform current density in a gear or other complex shaped component may require high current density and additional electrode contacts. Thus, in some instances, for example more complex parts like gear component 50, it is advantageous to utilize an AC current excitation and induce electric currents within the component. In the case of an AC signal, it is well known that the frequency of the AC signal and the conductivity of the component determine the penetration depth of the induced AC currents. By selecting an appropriate frequency, the induced currents will flow on and near the surface of the component. Accordingly, the thermal signature of the defect will be increased to a detectable level.

Figure 10A:
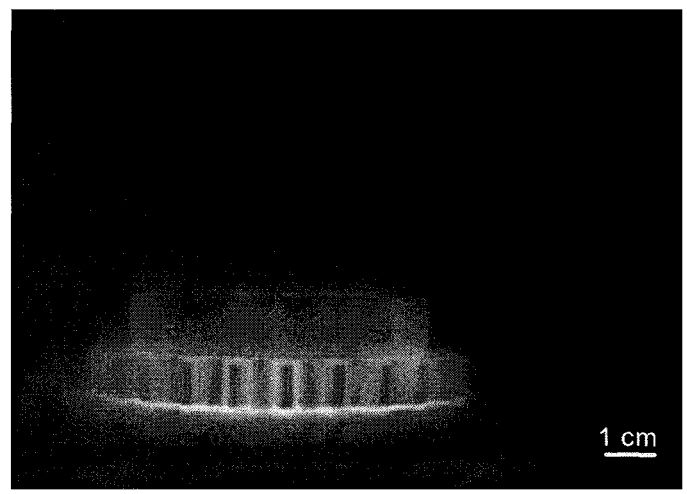
FIG. 10(a) shows an IR image from a gear component similar to that shown in FIG. 9, except without surface crack 42, which component has been subjected to inductive AC heating in the system 30 of FIG. 3.
Figure 10B:
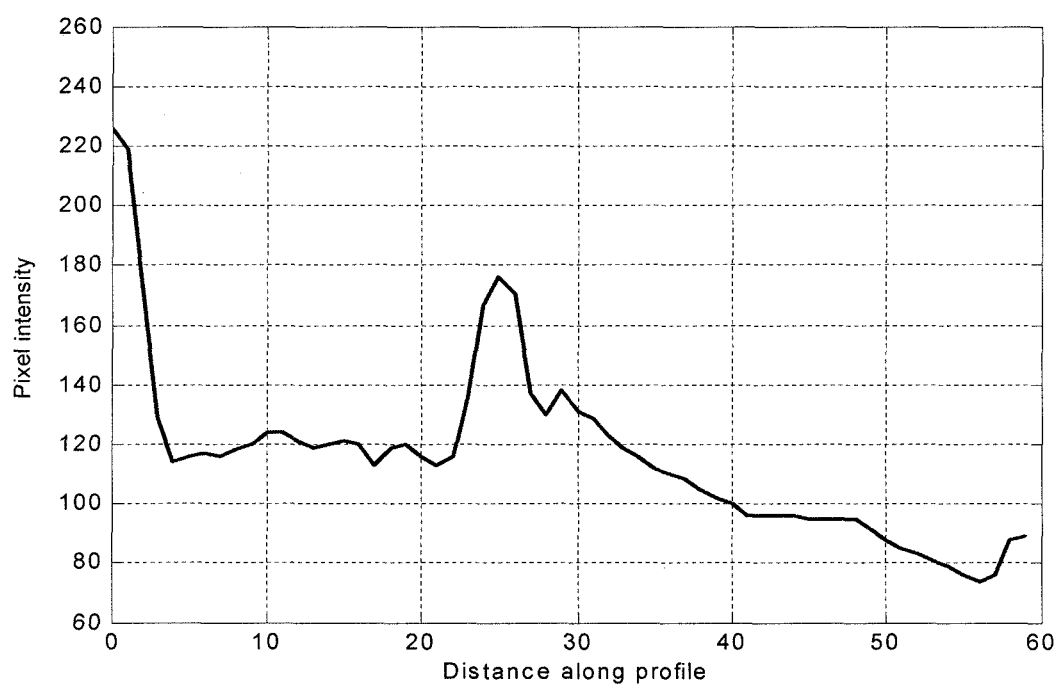
FIG. 10(b) shows a thermal profile taken along the dotted line 54 in FIG. 10(a)
Figure 11A:
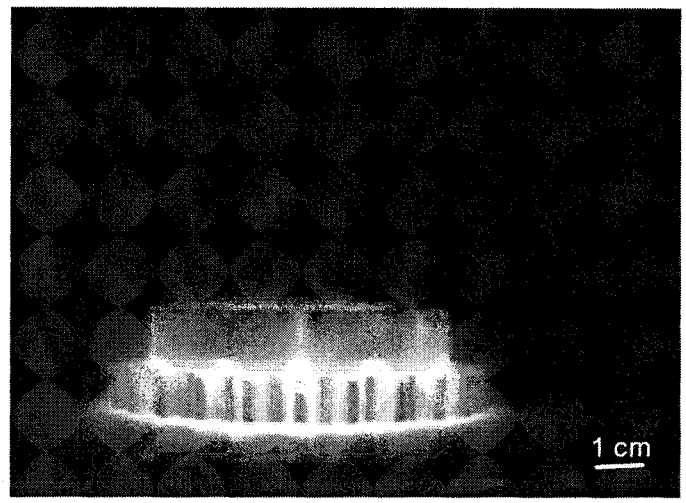
FIG. 11(a) shows an IR image of the defective gear component 50 shown in FIG. 9, which component has been subjected to inductive AC heating in the system 30 of FIG. 3.
Figure 11B:
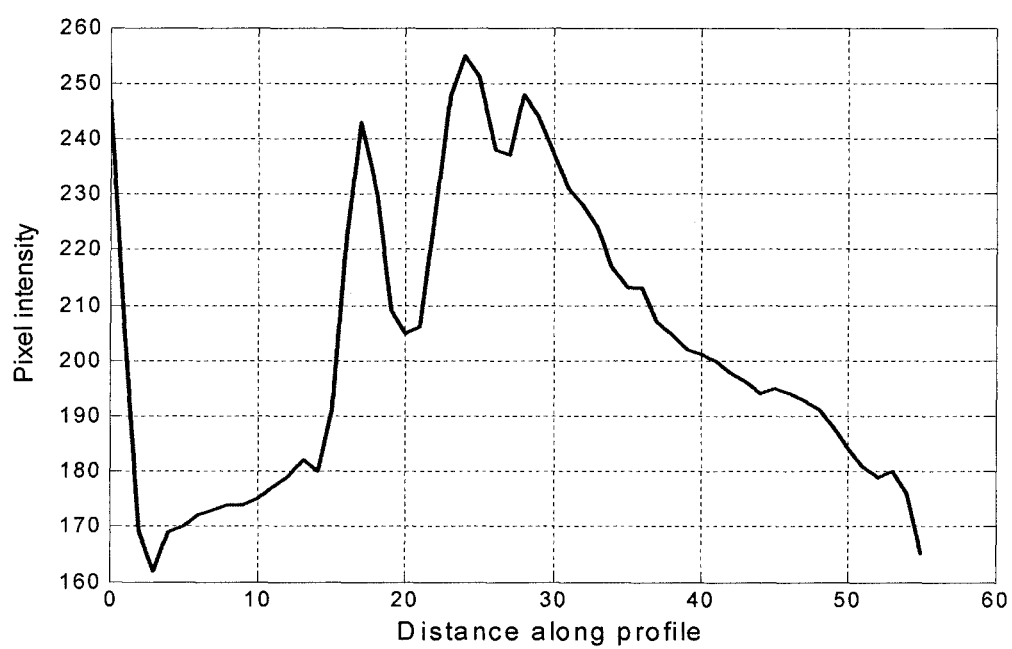
FIG. 11(b) shows a thermal profile taken through gear component 50 of FIG. 11(a) in a manner similar to the profile of FIG. 10(b)

FIG. 10 depicts infrared images for 2D surface and line profiles (along the dotted line). The data is collected with an IR camera positioned 50 cm away (viewed from the side) and operated at a frame rate of 30 Hz. The field of view of the 240 by 320 pixel picture is 15 cm by 15 cm. The total line length of 10 cm is subdivided into 180 points (i.e. with a point-to-point resolution of 0.5 mm) whereas the thermal pixel intensity is displayed in discrete increments up to a maximum discrete level of 260 (or 460K). FIG. 10(*b*) depicts a thermal profile of an un-defective gear part taken along the dotted line in FIG. 10(*a*). FIG. 11(*a*) depicts a defective gear part being heated by induction heating, and FIG. 11(*b*) depicts the thermal profile of the defective gear. A comparison of FIGS. 11(*b*) and 10(*b*) illustrates how the profile of a defective part differs from a un-defective part.

The present system and method is also appropriate for real time use on a manufacturing process as it maintains stable performance and is immune from temperature fluctuations in a plant arising from production equipment such as presses, motors, and sinter furnaces. In addition, the present system and method may be extended to detect defects regardless of material composition. For example, Aluminum powder presents a unique challenge as it is a highly reflective material with very low emissivity (0.1 to 0.2) when compared to steel parts with high graphite content where the emissivity is of the order of 0.6.

Because of the characteristics of the powdermetallic parts, it is also possible to passively test the parts without using an additional heating source or electric current. In this embodiment, the parts are imaged using the residual heat in the part as it exits from the manufacturing press system. In general this method uses the I/R camera, computer system and processing methods substantially similar in nature to the embodiments in which the parts have been heated using an electric current. This embodiment may also be used in conjunction with a conveyer system for automatic defect detection.

Figure 12:
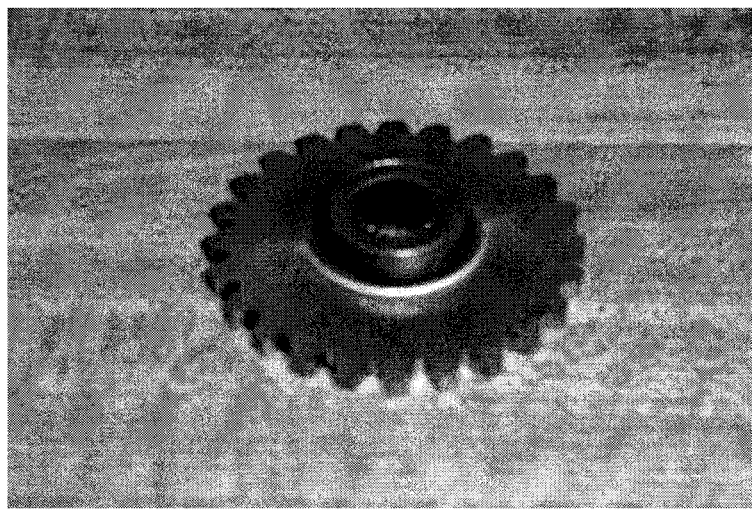
FIG. 12 is a picture of a green-state P/M part to be tested at a manufacturing facility.
Figure 13A:
FIG. 13(a) shows an IR image from the gear 50 of FIG. 12 at a speed of 0.3 m/s.
Figure 13B:
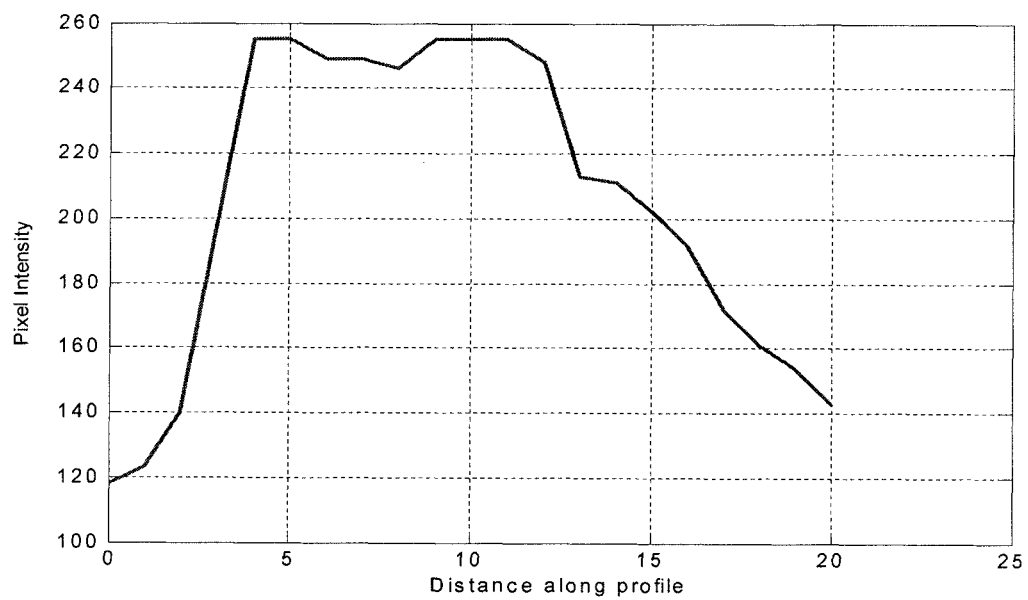
FIG. 13(b) shows a thermal profile along the dotted line.
Figure 14:
FIG. 14 shows a thermal image indicating the temperature monitoring point.

FIG. 12 shows the green-state steel P/M sample. The component is a two level gear with 13 mm in height by 60 mm in diameter and is typically manufactured at a rate of approximately 600 parts per hour, although parts per hour measured in the thousands are possible. FIGS. 13 and 14 depict 2-D surface and line profiles (recorded along the dotted line in FIG. 13(*a*)) of parts that are expected to be defect-free. The images are recorded with the IR camera positioned 50 cm away (viewed from the side) and operated at a frame rate of 30

Hz. The field of view of the 240 by 320 pixel viewing is 15 cm by 15 cm. The total line length of 10 cm is subdivided into 180 points (i.e. with a point-to-point resolution of 0.5 mm) whereas the thermal pixel intensity is displayed in discrete increments from a baseline of 0 (or 200K) to 260 (or 460K).

Figure 15:
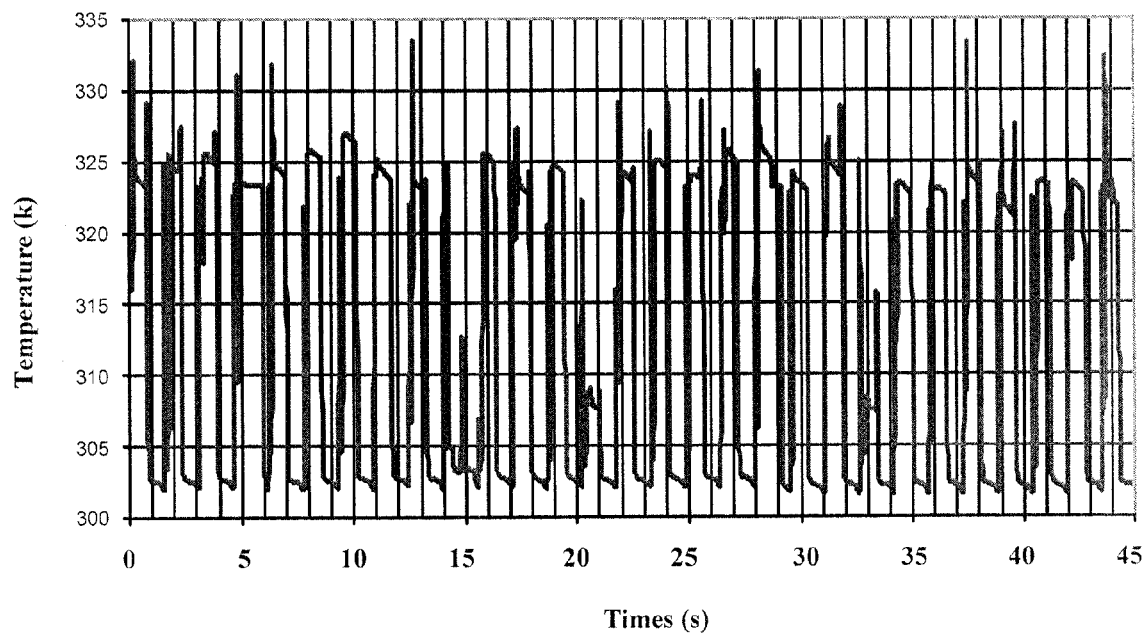
FIG. 15 shows a temperature plot (in K) of a single IR image pixel recorded over time for a production line of component P/M gears 50 without defects.

A long IR image sequence of 45 seconds recording duration generates 1350 recorded temperature sampling points with an intensity profile depicted in FIG. 15 (recorded along the tracking point depicted in FIG. 14). As expected, as soon as a component moves past the fixed spatial sensing location, the temperature increases.

Figure 16:
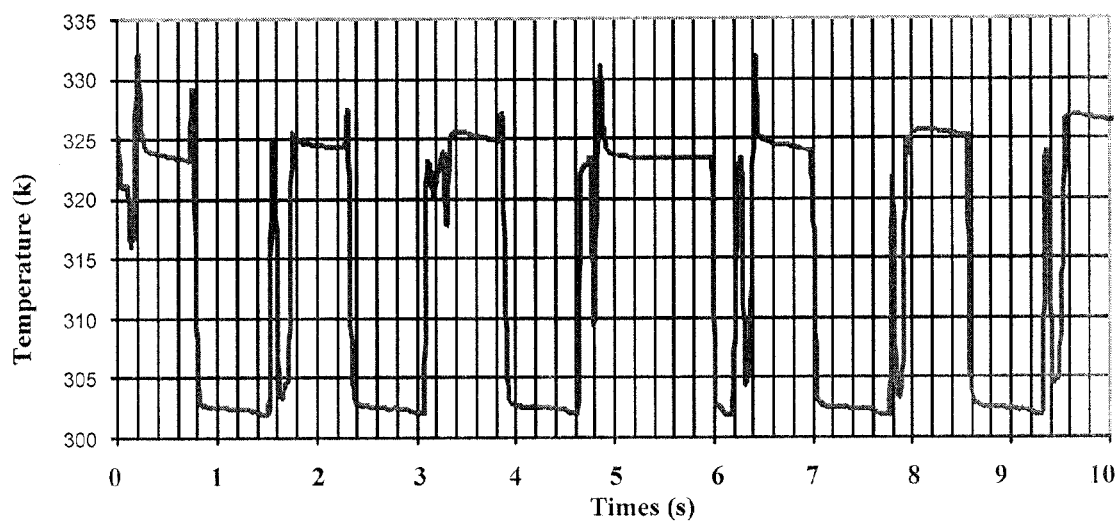
FIG. 16 shows a close-up view of a portion of the temperature plot of FIG. 15.

FIG. 16 depicts a portion of FIG. 15 that has been zoomed-in on; it allows a more detailed analysis to be performed on the graphical data. Apart from small variations, the temperature profiles are reproducible. This is consistent with the fact that the parts are defect-free. Therefore, we attribute these thermal fluctuations to instabilities in the industrial manufacturing process.

Figure 17A:
FIG. 17(a) shows a second image from the IR recording of the gear shown in FIG. 12, at a speed of 0.13 ms, and (b) thermal profile along the dotted line.
Figure 17B:
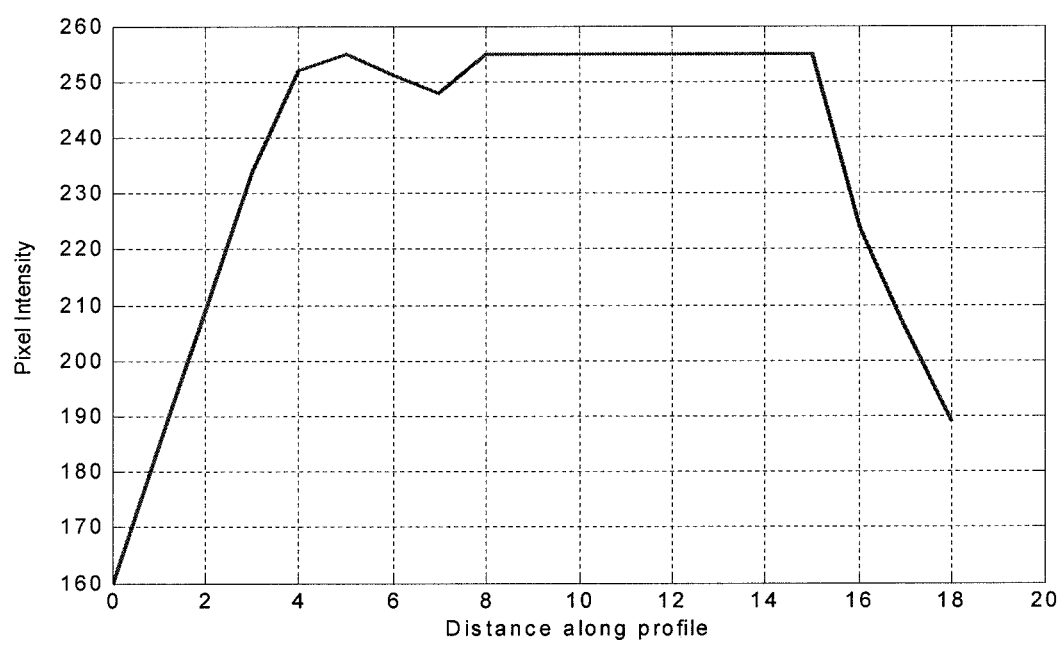
Figure 18:
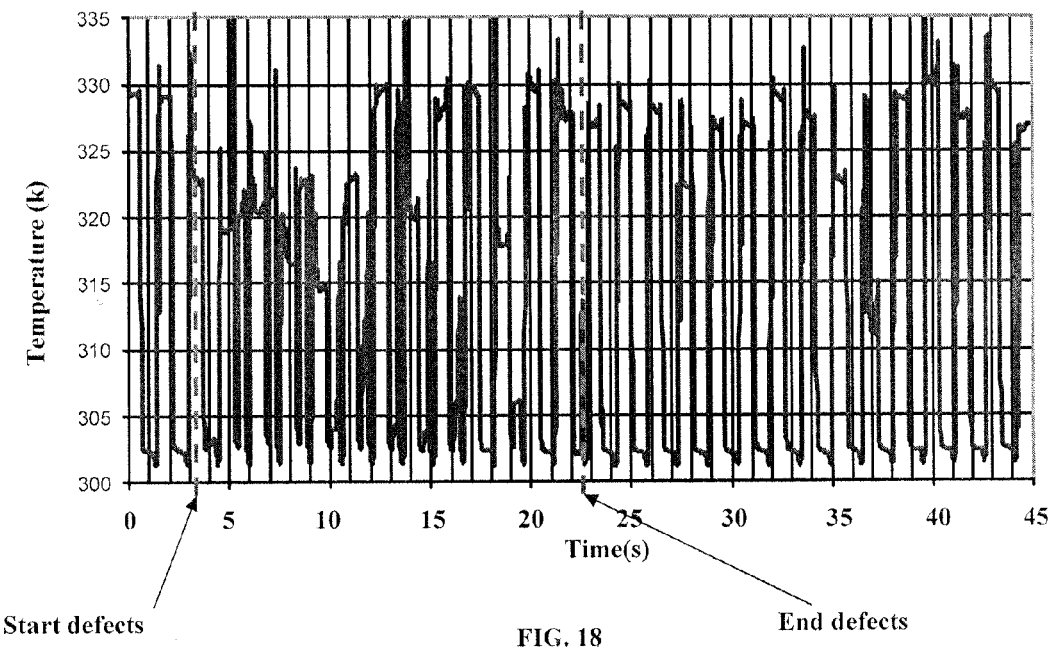
FIG. 18 shows a temperature plot (in K) of a single IR image pixel recorded over time for a production line of component P/M gears 50, wherein the componenting process is changed first to introduce defects into the gears and then changed again to produce gears without defects.
Figure 19:
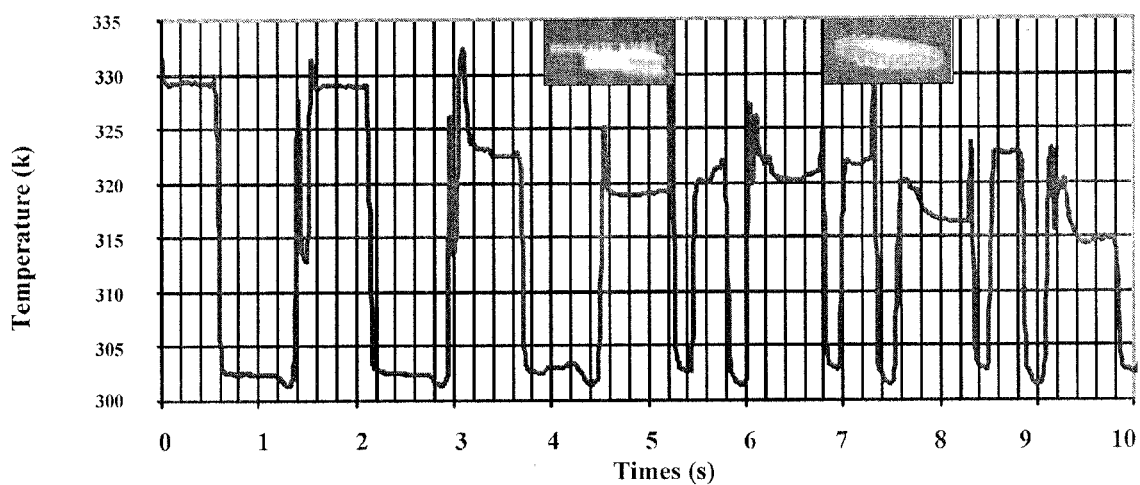
FIG. 19 is a close-up or zoomed-in view of the portion of the plot of FIG. 18, wherein defective parts are shown.

FIG. 17(*a*) depicts a second image of the gear depicted in FIG. 12 at a speed of 0.13 m/s and FIG. 17(*b*) shows a thermal profile along the dotted line. FIG. 18 shows an entire 45 sec inspection duration, or 1350 frames. Defects were introduced into the gears by changing press settings during press operations during the manufacturing of the gears. FIG. 18 identifies the points were the process was modified and the defects introduced. During the first 20 seconds we see defective parts and later, after the process adjustment, the response of defect-free parts. As depicted in FIG. 19, a magnified portion of FIG. 18 between 1 and 10 seconds, defects may be identified using, a simple subtraction technique as discussed above would be sufficient to flag defective components.

As can be seen by directly comparing FIG. 19 with FIG. 16, several parts are defective. As a result, this methodology has the potential of being a very simple, yet reliable methodology that allows the identification of defective parts in an on-line setting.

Figure 20:
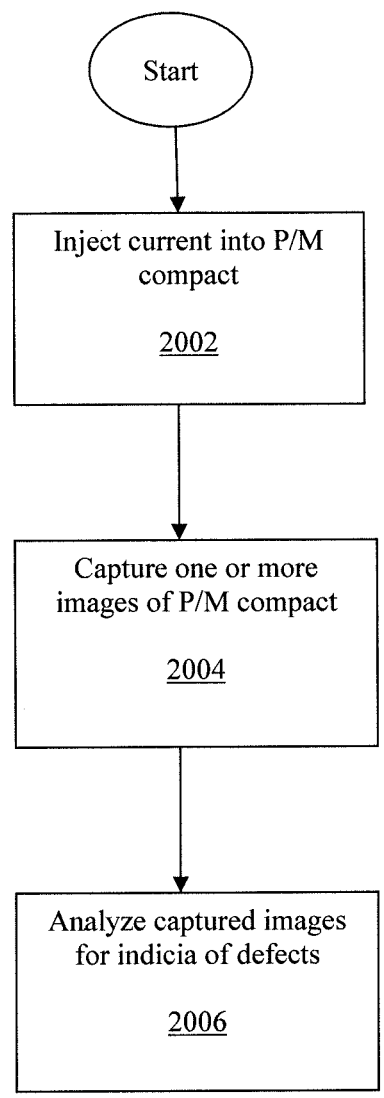
FIG. 20 depicts a flow chart illustrating a method of practicing the present invention.

FIG. 20 depicts a method for detecting defects in a powdermetallic component. In particular, the method includes the steps of: injecting an electric current into the powdermetallic component, step 2002. The injected current causes the powdermetallic component to heat; it produces a temperature change in the powdermetallic component. Capturing one or more infrared images of the heated powdermetallic component, step 2004, and analyzing the captured images to detect temperature differences, step 2006, where the detected temperature differences may be indicia of a defect in the powdermetallic component.

In the embodiment in which the parts to be examined are passed by the I/R camera, additional processing is necessary to ensure that the part is entirely within the image. One method to do this is to detect the part boundaries. Once the part is within the image area, image frames are taken and saved and processed as would be known in the art.

The current that is injected into the powdermetallic component method may be direct current or an alternating current. The current is to be maintained substantially constant throughout the powdermetallic component. If the component is a simple design, direct current is typically used, but where the component is a more complex shape, such as a gear, alternating current is used, where the frequency of said alternating current is selected to provide a desired penetration depth of said alternating current into the powdermetallic component. In the embodiment in which alternating current is utilized, induction rather than direct physical contact may be used to inject the alternating current into the component. The analyzing of the captured infrared image may include determining the thermal gradient contained on two or more profiles defined on the surface of the component and separating the thermal gradients generated by a defect from other effects by subtracting the first profile thermal gradient from a second profile thermal gradient. In addition, the analysis of the data includes determining the derivative of a thermal profile of one or more preselected areas on the surface of the powdermetallic component. In another embodiment, the analysis of the thermal data may include determining the Laplacian of the thermal profile of one or more preselected areas on the surface of said powdermetallic component.

While the pulsed thermography defect detection system has been described in detail and with reference to specific embodiments thereof, it will be apparent to those skilled in the art that various changes and modifications can be made therein without departing from the spirit and scope thereof. Thus, it is intended that the appended claims, and their equivalents, define the invention.

What is claimed is:

1. A pulsed thermography apparatus for testing a powdermetallic component, the apparatus comprising:
    a power source coupled to the powdermetallic component and operative to provide an electric current within the powdermetallic component, wherein said powdermetallic component when heated by said electric current emits infrared radiation that varies according to temperature;
    a timing unit coupled to said power source;
    a switch operative to control the electric current;
    a first contact and a second contact coupled to said power source, the powdermetallic component being disposed between and electrically coupled to said first contact and said second contact, said first contact and said second contact each sized and configured to provide substantially uniform current flow into the powdermetallic component;
    a press drive system coupled to at least said first contact and operative to provide biasing force against said at least said first contact to maintain constant and consistent electrical connectivity between said at least said first contact and the powdermetallic component;
    an infrared camera optically coupled to the powdermetallic component and configured to record an image thereof, said image based on the infrared radiation emitted therefrom, said infrared camera further coupled to said function generator, wherein said function generator is operative to control the recording of said image by said infrared camera; and
    a signal processing system coupled to said infrared camera and operative to receive said recorded image therefrom, said signal processing system further coupled to said power source, wherein said signal processing system receives said recorded image from said infrared camera and processes said recorded image to detect flaws in the powdermetallic component based on thermal response recorded over time.

2. The apparatus of claim 1 wherein the power source is a direct current (DC) current source.

3. The apparatus of claim 2 wherein said switch includes a control input for controlling the conductivity of said switch and wherein said timing unit is coupled to said switch.

4. The apparatus of claim 1 wherein the timing unit comprises a function generator which provides a control pulse to said control input of said switch and to said infrared camera, wherein said leading edge of said control pulse triggers said infrared camera to begin recording and triggers said switch to conduct said electric current.

5. The apparatus of claim 1 wherein said switch is a solid state switching device.

6. The apparatus of claim 5 wherein the solid state switching device is a MOSFET.

7. A pulsed thermography apparatus for testing a powdermetallic component, the apparatus comprising:
    a power source coupled to the powdermetallic, component, said power source being an alternating current (AC) current source, wherein said AC current has a frequency and said frequency is selected to provide a desired depth of penetration of said current in the powdermetallic component and operative to provide an electric current within the powdermetallic component, wherein said powdermetallic component when heated by said electric current emits infrared radiation that varies according to temperature;
    a timing unit operative to control the electric current;
    an induction coil coupled to said power source, wherein said power source provides said AC current to said induction coil and said induction coil is operative to induce electric currents in the powdermetallic component;
    an infrared camera optically coupled to the powdermetallic component and configured to record an image thereof, said image based on the infrared radiation emitted therefrom, said infrared camera further coupled to said timing unit, wherein said timing unit is operative to control the recording of said image by said infrared camera; and
    a signal processing system coupled to said infrared camera and operative to receive said recorded image therefrom, said signal processing system further coupled to said power source, wherein said signal processing system receives said recorded image from said infrared camera and processes said recorded image to detect flaws in the powdermetallic component based on thermal response recorded over time.

8. The apparatus of claim 1, wherein said press drive system provides biasing force against said first contact and said second contact to maintain electrical connectivity between said first contact and said second contact and the powdermetallic component.

9. The apparatus of claim 7 wherein the timing unit provides a timing pulse, wherein the leading edge of said timing pulse is operative to trigger said power source to provide said AC current and for said infrared camera to begin recording images of the powdermetallic component.

10. The apparatus of claim 7 further including an insulating platform disposed between said induction coil and said powdermetallic component.

11. The apparatus of claim 10 wherein the insulating platform includes a conveyer belt for passing powdermetallic component parts passed said I/R, camera.

12. The apparatus of claim 1 wherein said signal processing system is operative to process said received image using threshold processing.

13. The apparatus of claim 12 wherein said signal processing system is operative to process said received image using profile processing.

14. The apparatus of claim 13 wherein said profile processing includes using two or more profiles on said surface of said powdermetallic component and separating thermal gradients generated by said defects from other effects by subtracting a first profile thermal gradient from a second profile thermal gradient.

15. The apparatus of claim 14 wherein said signal processing system is operative to process said received image using profile processing.

16. The apparatus of claim 15 wherein said profile processing includes using two or more profiles on said surface of said powdermetallic component and separating thermal gradients generated by said defects from other effects by subtracting a first profile thermal gradient from a second profile thermal gradient.

17. The apparatus of claim 15 wherein said profile processing includes using threshold defect detection.

18. The apparatus of claim 1 wherein said signal processing system is operative to process said received image calculating a derivative of a thermal profile of a plurality of preselected areas on a surface of said powdermetallic component.

19. The apparatus of claim 1 wherein said signal processing system is operative to process said received image calculating a laplacian of a thermal profile of a plurality of preselected areas on a surface of said powdermetallic component.

20. The apparatus of claim 5 wherein the solid state switching device is a IGBT.

* * * * *